United States Patent
Mirjalili et al.

(10) Patent No.: US 12,099,261 B2
(45) Date of Patent: Sep. 24, 2024

(54) ESTIMATING A MENTAL STATE BASED ON SENSOR MEASUREMENTS FROM AN ELECTRONIC CONTACT LENS

(71) Applicant: Tectus Corporation, Saratoga, CA (US)

(72) Inventors: Ramin Mirjalili, San Jose, CA (US); Abhishek Deepak Bhat, Santa Clara, CA (US)

(73) Assignee: TECTUS CORPORATION, Cupertino, CA (US)

( * ) Notice: Subject to any disclaimer, the term of this patent is extended or adjusted under 35 U.S.C. 154(b) by 656 days.

(21) Appl. No.: 17/398,267

(22) Filed: Aug. 10, 2021

(65) Prior Publication Data

US 2023/0051444 A1    Feb. 16, 2023

(51) Int. Cl.
| | |
|---|---|
| *G02C 7/08* | (2006.01) |
| *A61B 5/00* | (2006.01) |
| *A61B 5/16* | (2006.01) |
| *A61B 5/18* | (2006.01) |
| *G02C 7/04* | (2006.01) |
| *G02C 11/00* | (2006.01) |
| *G01K 13/20* | (2021.01) |

(Continued)

(52) U.S. Cl.
CPC .............. *G02C 7/083* (2013.01); *A61B 5/163* (2017.08); *A61B 5/18* (2013.01); *A61B 5/4845* (2013.01); *A61B 5/746* (2013.01); *G02C 7/04* (2013.01); *G02C 11/10* (2013.01); *G01K 13/20* (2021.01); *G01P 15/14* (2013.01); *G01R 33/1215* (2013.01)

(58) Field of Classification Search
CPC .......... G02C 7/083; G02C 7/04; G02C 11/10; A61B 5/163; A61B 5/18; A61B 5/4845; A61B 5/746; A61B 5/02055; A61B 5/1102; A61B 5/6821; A61B 2562/0219; A61B 5/4815; G01K 13/20; G01P 15/14; G01R 33/1215

See application file for complete search history.

(56) References Cited

U.S. PATENT DOCUMENTS

| | | | |
|---|---|---|---|
| 10,948,988 B1 | 3/2021 | Wiemer | |
| 11,619,994 B1 * | 4/2023 | Bhat | ........................ G02C 7/04 345/156 |

OTHER PUBLICATIONS

Abnormal Eye Movements in Parkinsonism and Movement Disorders, Jung et al., J Mov Disord 2019;12(1):1-13.

(Continued)

*Primary Examiner* — James C. Jones
(74) *Attorney, Agent, or Firm* — AMSEL IP LAW PLLC; Jason Amsel

(57) ABSTRACT

A system includes an electronic contact lens that obtains sensor measurements from integrated motion sensors or other types of sensors and a processing module that estimates a mental state of an individual based on the sensor measurements. The processing module identifies patterns of eye movements and analyzes how these patterns change over time. Based on anatomical relationships between eye movement and mental state, the processing module estimates characteristics of the individual such as fatigue, intoxication, injury, or a medical condition that have known effects on eye movement patterns. The electronic contact lens system generates an output indicative of the estimated mental state to alert the individual to the detected condition or to initiate an automated action.

20 Claims, 18 Drawing Sheets

(51) Int. Cl.
  *G01P 15/14* (2013.01)
  *G01R 33/12* (2006.01)

(56) References Cited

OTHER PUBLICATIONS

Abnormalities of saccadic eye movements in dementia due to Alzheimer's disease and mild cognitive impairment, Wilcockson, et al., Aging v11, n15, p. 5389 (2019).
Association of Visual Tracking Metrics With Post-concussion Symptomatology, Maruta et al., Frontiers in Neurology, article 611, v9, Jul. 2018.
Effects of driving time on microsaccadic dynamics, Di Stasi, et al., Exp Brain Res (2015) 233:599-605.
Eye Movements in Alzheimer's Disease, Molitor, et al., Alzheimers Dis. 2015 ; 44(1): 1-12. doi:10.3233/JAD-141173.
Eye Tracking Detects Disconjugate Eye Movements Associated with Structural Traumatic Brain Injury and Concussion, Samadani et al., Journal of Neurotrauma 32:548-556 (Apr. 15, 2015).
Eye-Movement behavior identification for AD diagnosis, J. Biondi et al., arXiv:1702.00837v3 [cs.NE] (2018).
Fixation stability as a biomarker for differentiating mild traumatic brain injury from age matched controls in pediatrics, Hunfalvay et al., Brain Injury, DOI: 10.1080/02699052.2020.1865566 (2020).
Horizontal gaze nystagmus: a review of vision science and application issues, S. Rubenzer et al., J. Forensic Sci., 2010.
Microsaccade and drift dynamics reflect mental fatigue, Di Stasi, et al., European Journal of Neuroscience, pp. 1-10, 2013.
Nystagmus during Attacks of Vestibular Migraine: An Aid in Diagnosis, Polensek, et al., Audiol Neurotol 2010;15:241-246.
Oculomotor impairment after 1 night of total sleep deprivation: a dissociation between measures of speed and accuracy, De Gennaro, et al., Clinical Neurophysiology 111 (2000) 1771-1778.
Overlapping Saccades and Glissades are Produced by Fatigue in the Saccadic Eye Movement System, Bahill and Stark, Experimental Neurology, v48, p. 95-106, 1975.
Reflexive and Intentional Saccadic Eye Movements in Migraineurs, Filippopulos, et al., Frontiers in Neurology, article 669922, v12, Apr. 2021.
Saccadic Eye Movement Metrics Reflect Surgical Residents' Fatigue, Di Stasi, et al., Annals of Surgery, vol. 00, No. 00, p. 1-6, 2013.
Saccadic velocity as an arousal index in naturalistic tasks, Di Stasi et al., Neuroscience and Biobehavioral Reviews 37 (2013) 968-975.
Screening for Dyslexia Using Eye Tracking during Reading, M. Benfatto, et al., PLOS ONE, DOI:10.1371/journal.pone.0165508 (2016).
Sensitivity and specificity of an eye movement tracking based biomarker for concussion, Samadani, et al., Concussion (2015) 10.2217/CNC.15.3.
Spontaneous eyelid movements during human sleep: a possible ponto-geniculo-occipital analogue?, Conduit, et al., J. Sleep Res. (2002) 11, 95-104.
The Main Sequence, A Tool for Studying Human Eye Movements, Bahill, Clark, and Stark, Mathematical Biosciences, v24, p. 191-204, 1975.
Towards a driver fatigue test based on the saccadic main sequence: A partial validation by subjective report data, Di Stasi et al., Transportation Research Part C 21 (2012) 122-133.

\* cited by examiner

Saccade rate, and blink rate

| Normal | Abnormal |
|---|---|
| 1.28 (SD 0.31) saccades per second | 1.08 (SD 0.37) saccades per second |
| 0.18(SD 0.09) blink per second | 0.25 (SD 0.08) blink per second |

Fig. 8

Accelerometer can capture Heart-rate induced motion

Frequency analysis discriminates between HR and other motions by searching for 1st, 2nd, 3rd, ... harmonics

ESTIMATING A MENTAL STATE BASED ON SENSOR MEASUREMENTS FROM AN ELECTRONIC CONTACT LENS

BACKGROUND

1. Technical Field

This disclosure relates generally to estimating a mental state of an individual based on sensor measurements from an electronic contact lens.

2. Description of Related Art

An electronic contact lens may include various integrated electronic components such as projectors, imaging devices, sensors, and batteries. These electronic contact lenses can be utilized for virtual reality or augmented reality applications in which images are projected by the electronic contact lens onto the user's retina to replace or augment the user's view of the external environment. Integrated sensors in such electronic contact lenses may furthermore measure motion data associated with eye movements that can be used for a variety of purposes.

BRIEF DESCRIPTION OF THE DRAWINGS

FIG. 8 is a diagram illustrating changes in saccade rate and blink rate between normal and abnormal mental states.

DETAILED DESCRIPTION

A system includes an electronic contact lens that obtains sensor measurements from integrated motion sensors (or other types of sensors) and a processing module that estimates a mental state of an individual based on the sensor measurements. The processing module identifies patterns of eye movements and analyzes how these patterns change over time. Based on anatomical relationships between eye movement and mental state, the processing module estimates characteristics of the individual such as fatigue, intoxication, injury/trauma, mood, sleep quality, or a medical condition that have known effects on eye movement patterns. The electronic contact lens system generates an output indicative of the estimated mental state to alert the individual to the detected condition or to initiate an automated action in the electronic contact lens or an external device.

Eye movement patterns naturally vary between different individuals and in different contexts. To learn the normal eye movement patterns for different individuals under different situations, the electronic contact lens tracks and aggregates sensor data for an individual over an extended time period and under a variety of conditions. The electronic contact lens system also detects and tracks the conditions under which sensor measurements are captured and stores contextual data describing the conditions together with the sensor data. Based on the tracked sensor measurements and contextual data, the processing module generates one or more baseline eye motion parameters for an individual that each represent normal eye motion patterns for that individual under the different conditions. The processing module may then detect significant deviations from these established baselines to identify changes that are indicative of an abnormal mental condition.

The processing module may generate various alerts based on the detected conditions. For example, the processing module may cause the electronic contact lens to display visual notifications (using an integrated femtoprojector) or output audio notifications to alert the individual to the detected condition. Alternatively, the processing module can send the alerts to an external device such as a smart phone, tablet, or other computing system.

Figure 1A:
FIG. 1A shows a user wearing an electronic contact lens.
Figure 1B:
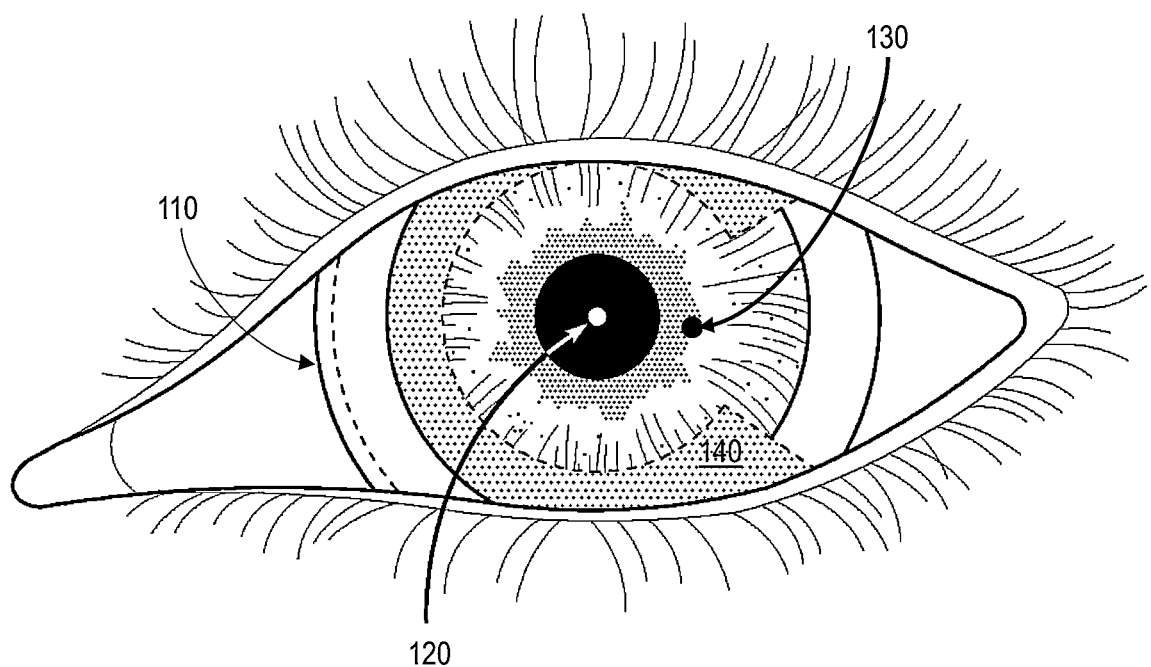
FIG. 1B shows a magnified and simplified view of the electronic contact lens mounted on the user's eye.
Figure 1C:
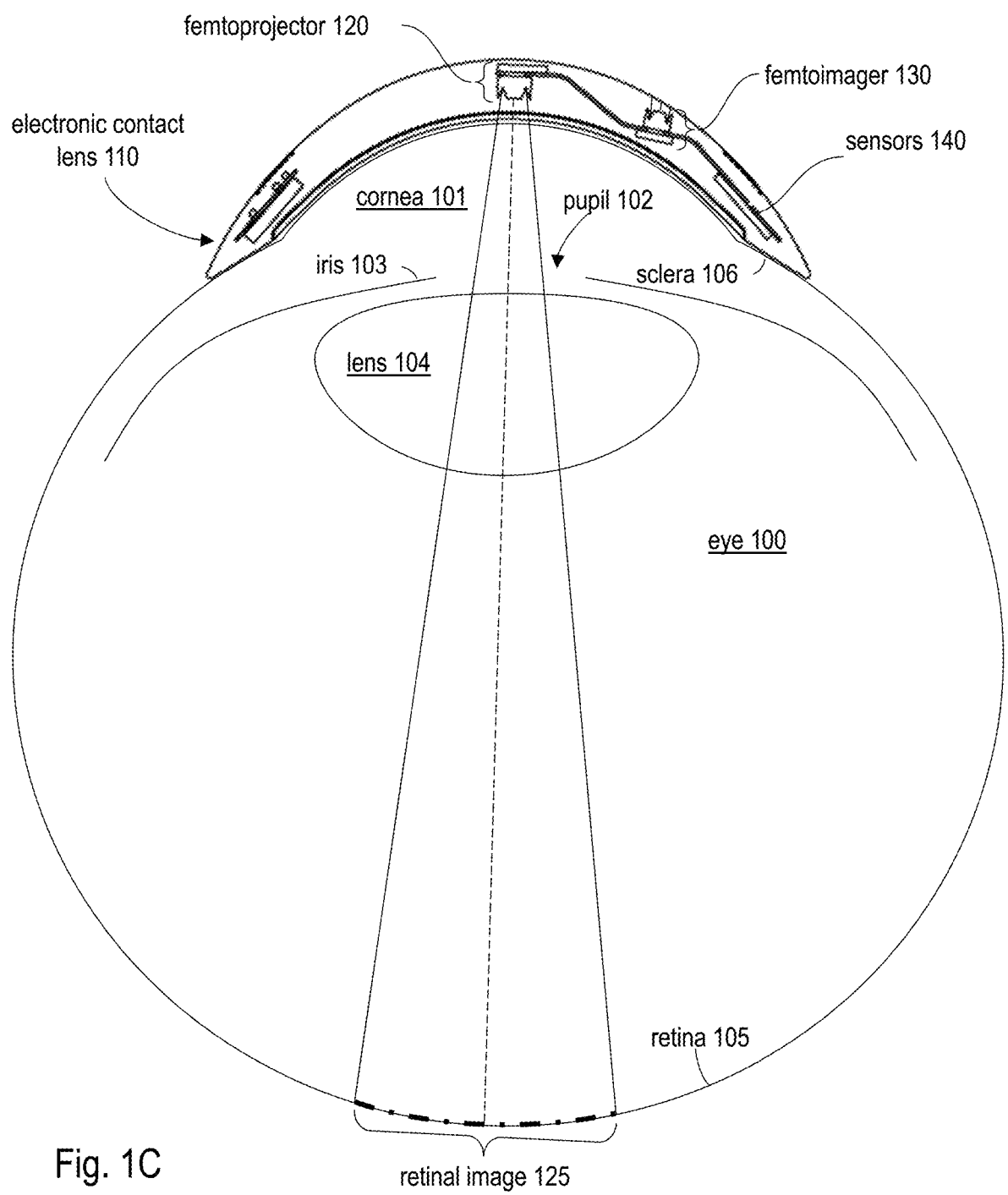
FIG. 1C shows a cross sectional view of the electronic contact lens mounted on the user's eye.

FIG. 1A shows a user wearing a pair of electronic contact lenses 110. In other instances, the user may wear only a single electronic contact lens 110 in just one eye. FIG. 1B shows a magnified view of an electronic contact lens 110, and FIG. 1C shows a cross sectional view of the electronic contact lens 110. The following examples use a scleral contact lens in which the contact lens is supported by the sclera of the user's eye, but the contact lens does not have to be scleral.

As shown in FIG. 1B, the electronic contact lens 110 contains a femtoprojector 120, a femtoimager 130, and sensors 140. The femtoprojector 120 and femtoimager 130 are optional, and in other embodiments, the electronic contact lens 110 may omit these components.

The optional femtoprojector 120 is a small projector that projects images inward onto the user's retina. It is located in a central region of the contact lens 110, so that light from the femtoprojector 120 propagates through the user's pupil to the retina. The femtoprojector 120 typically includes an electronics backplane (e.g., driver circuitry), a frontplane of light emitting elements (e.g., an LED array) and projection optics. The frontplane produces an image (referred to as the source image), which is optically projected by the projection optics through the various eye structures and onto the retina 105, as shown in FIG. 1C.

The optional femtoimager 130 is a small imager that is outward facing and captures images of the external environment. In this example, it is located outside the central region of the contact lens 110 so that it does not block light from entering the user's eye. The femtoimager 130 typically includes imaging optics, a sensor array, and sensor circuitry. The imaging optics images a portion of the external environment onto the sensor array, which captures the image. The sensor array may be an array of photosensors. In some embodiments, the sensor array operates in a visible wavelength band (i.e., ~390 nm to 770 nm). Alternatively or additionally, the sensor array operates in a non-visible wavelength band, such as an infrared (IR) band (i.e., ~750 nm to 10 μm) or an ultraviolet band (i.e., <390 nm). For example, the sensor array may be a thermal infrared sensor.

The femtoprojector 120 and femtoimager 130 typically are not larger than 2 mm wide. They may fit within a 2 mm×2 mm×2 mm volume. In an embodiment, the electronic contact lens 110 has a thickness that is less than two millimeters.

The sensors 140 and other associated electronics may be mounted on a flexible bus located in a peripheral zone of the electronic contact lens 110. The sensors 140 may include motion sensors such as an accelerometer and a gyroscope. The sensors 140 may furthermore include a magnetometer and additional sensors such as temperature sensors, light sensors, and audio sensors. Sensed data from the sensors 140 may be combined to estimate parameters such as position, velocity, acceleration, orientation, angular velocity, angular acceleration or other motion parameters of the eye. For example, in one embodiment, gyroscope data may be filtered based on magnetometer data and accelerometer data to compensate for drift in the gyroscope data. In another embodiment, gyroscope data may be filtered based on temperature data to reduce temperature bias associated with the gyroscope data.

The motion sensors 140 may collect sensed data in an ongoing manner so that the sensor measurements may cover a relatively long history (e.g., days, weeks, years). Because the motion sensors 140 are mounted directly on the eye, the motion sensors 140 may capture movements even when the eye is closed.

The electronic contact lens 110 may furthermore include various other electronic components (not shown) such as a radio transceiver, power circuitry, an antenna, a battery, or inductive charging coils. The electronic contact lens 110 may also include cosmetic elements, for example covering the motion sensors 140 or other electronic components. The cosmetic elements may be surfaces colored to resemble the iris and/or sclera of the user's eye.

FIG. 1C shows a cross sectional view of the electronic contact lens mounted on the user's eye. FIG. 1C illustrates some structures of the eye 100 including the cornea 101, pupil 102, iris 103, lens 104, retina 105, and sclera 106. The contact lens 110 maintains eye health by permitting oxygen to reach the cornea 101.

As shown in FIG. 1C, the optional femtoimager 130 is outward-facing, so that it captures images of the surrounding environment, while the optional femtoprojector 120 is inward-facing and projects an image 125 onto the user's retina 105. The femtoimager 130, femtoprojector 120, and sensors 140 all move together with the eye 100 because the electronic contact lens 110 is physically mounted to the eye 100. Thus, the sensors 140 naturally capture motion of the eye. Furthermore, images captured by the femtoimager 130 naturally have a line of sight corresponding to the user's gaze direction and virtual images projected by the femtoprojector 120 naturally move together with the eye 100.

Figure 2:
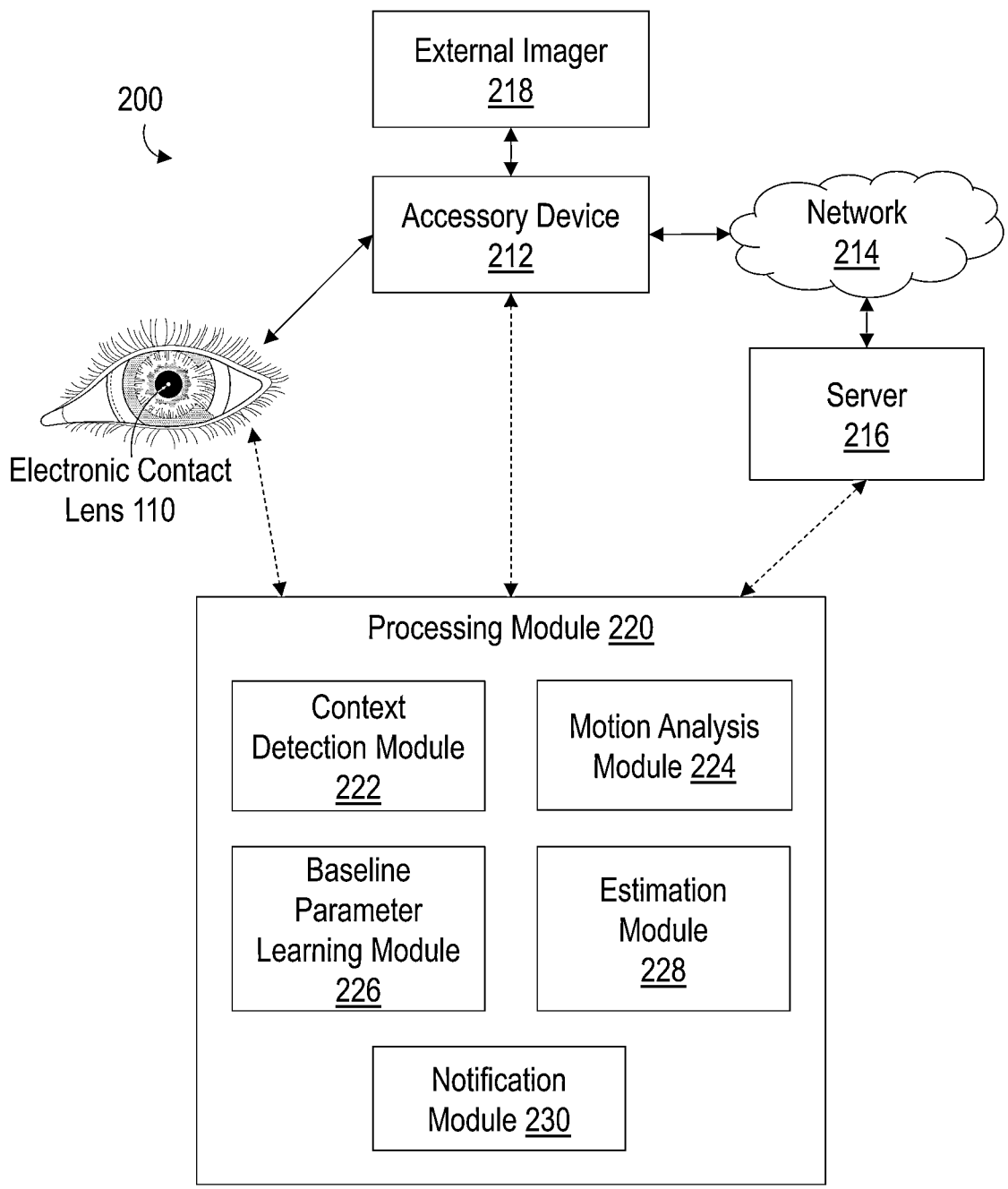
FIG. 2 is a block diagram of an electronic contact lens system.

FIG. 2 shows a block diagram of an electronic contact lens system 200. The electronic contact lens system 200 includes the electronic contact lens 110, as described above, an accessory device 212, a network 214, a server 216, and an optional external imager 218. The accessory device 212 is a computing device that is communicatively coupled to the electronic contact lens 110 (e.g., via a wireless interface) and performs computing or storage functions that support operation of the electronic contact lens 110. The accessory device 212 may be embodied as an electronic wearable device (e.g., necklace, headband, waistband, etc.), smartphone, smart-watch or another device. The accessory device 212 may also be connected to a server 216 via a network 214. The server 216 provides access to various information relevant to operation of the electronic contact lens 110 and may furthermore provide additional computing or storage functions that support operation of the electronic contact lens 110. The external imager 218, if present, captures images of the external environment and may be used to supplement images captured by the optional femtoimager 130 of the electronic contact lenses 110. The external imager 218 may capture images having a wider field of view, higher resolution or other improved image characteristics relative to the images captured by the femtoimager 130.

A processing module 220 interfaces with the electronic contact lens 110 to track and analyze motion data, generate estimates relating to a mental state based on the analyzed motion data, and generate various notifications relating to the estimates. The processing module 220 may furthermore generate contextual data relating to captured sensor measurements and perform other functions of the electronic contact lens 110 such as generating virtual images for display using the femtoprojector 120, processing images obtains from the femtoimager 130, or other tasks.

Various components of the processing module 220 may be implemented in whole or in part in the electronic contact lens 110, the accessory device 212, the server 216, or a combination thereof. In some implementations, certain time-sensitive functions of the processing module 220 may be implemented directly on the electronic contact lenses 110 for low latency while other more computationally intensive functions may be offloaded to the accessory device 212 or to the server 216 to enable the electronic contact lens 110 to operate with relatively light computational and storage requirements. For example, in one implementation, the electronic contact lens 110 transfers the raw sensor data to the accessory device 212 for processing. The accessory device 212 may process the data directly or may offload one or more functions in whole or in part to the server 216. Alternatively, the electronic contact lens 110 may perform some lightweight initial processing on the sensor data and send the initially processed sensor data to the accessory device 212. For example, the electronic contact lens 110 may perform some filtering or compression of the sensor data. Responsibility for other tasks such as generating virtual images and processing captured image data may similarly be shared between the electronic contact lenses 110, accessory device 212, and server 216 in different ways.

The processing module 220 includes a context detection module 222, a motion analysis module 224, a baseline parameter learning module 226, a estimation module 228, and a notification module 230. Other embodiments may include different, additional, or fewer components.

The context detection module 222 generates contextual data relating to the circumstances under which the sensors 140 acquire sensor measurements. For example, the context detection module 222 may detect information such as an identity of the subject wearing the electronic contact lens 110, a physical state of the subject, or environmental conditions where the subject is located. The captured contextual data may include profile information associated with the subject (e.g., demographic information, biometric information, health information, etc.), a geographic location of the electronic contact lens 110, a timestamp associated with sensor measurements (including time of day, time of year, etc.), an environment (such as whether the subject is inside a building, driving a vehicle, or outdoors), an activity being performed by the subject (e.g., sitting, standing, laying down, sleeping, walking, playing a sport, working, etc.), ambient conditions (e.g., weather), objects in the vicinity of the subject and their level of activity, level of visual stimulus in the vicinity of the subject (e.g., whether the subject is viewing a busy bus terminal or a serene landscape), or other contextual data. The contextual data may be obtained using a variety of different techniques. For example, some contextual data may be obtained directly from the user via manual inputs. Other information may be obtained from a profile stored to the accessory device 212 or the server 216. Information may also be obtained by querying various web services (e.g., such as weather information services, location services, etc.). The context detection module 222 may also estimate conditions by performing content recognition on images captured by a femtoimager 130 of the electronic contact lens 110 or external imager 218. For example, the context detection module 222 may use images to detect the environment of the subject, whether the subject is in a high activity or low activity environment, etc. The captured contextual data is stored together with the concurrently captured sensor measurements.

The motion analysis module 224 analyzes sensor measurements from the electronic contact lens 110 to generate one or more motion parameters characterizing eye motion. Here, the motion analysis module 224 may apply various filters and/or functions to the raw sensor data (e.g., from the accelerometer, gyroscope, magnetometer, thermometer, or other sensors) to detect certain types of eye movements and characterize those eye movements. Examples of detectable eye movements include saccades, overlapping saccades, microsaccades, smooth pursuits, drift, and fixations. The parameters characterizing these motions may comprise, for example, counts of different movement types, rates at which the movement types occur, velocities or accelerations occurring during specific movements, time between movements, or other characteristics. The motion analysis module 224 may furthermore track basic eye movements like changes in yaw (horizontal movement), pitch (vertical movement), and roll (rotation about the gaze axis). In an embodiment, the motion analysis module 110 may track motions occurring even when the eyes are closed (e.g., while blinking and while sleeping). The motion analysis module 224 may be specifically configured to compute motion parameters that are correlated with a mental state of a subject as described in further detail below in FIGS. 3-11.

The baseline parameter learning module 226 estimates one or more baseline parameters (which may each relate to different subject, contexts, or both) representing motion patterns or other parameters captured over a relatively long time period (e.g., days, weeks, months, or years). The baseline parameter learning module 226 may generate the baseline parameters directly from sensor measurements or from the parameters computed by the motion analysis module 224. Each baseline parameter comprises a metric describing a specific aspect of eye motion (or other sensed characteristic) under a baseline (e.g., normal) mental condition.

Each baseline parameter may be estimated from a specific filtered subset of the sensor measurements. For example, a subject-specific baseline parameter for an individual may be estimated using a filtered dataset containing only sensor measurements pertaining to that individual. Furthermore, a baseline parameter relating to a specific environment (e.g., driving a vehicle) may be estimated using a filtered dataset containing only sensor measurements associated with that specific environment. In a further example, baseline parameters may be computed based on a filtered dataset that has been filtered to remove outliers or filtered based on some other statistical function. The baseline parameters may be re-computed or updated in real-time or periodically as additional sensor measurements are captured. The baseline parameters are stored together with relevant contextual data describing the sensor measurement dataset from which the baseline parameter was computed so that different baselines may be user-specific and/or context-specific.

In other instances, baseline parameters may be obtained from external inputs instead of being learned from sensor measurements. For example, some baseline parameters may comprise fixed or dynamically updated universal parameters that are obtained from some external source (e.g., a storage medium or web service). In these cases, the baseline parameters are not necessarily user-specific or context-specific and may be based on universally applicable values relevant to wide ranges of individuals and contexts.

The estimation module 228 estimates a mental state of a subject based on a set of recently captured sensor measurements (and/or parameters estimated from those measurements), corresponding contextual data, and stored baseline parameters. Here, the estimation module 228 may estimate the mental state as being abnormal when a current eye parameter computed based on a set of recent sensor measurements deviates significantly from a relevant baseline parameter.

The notification module 230 generates notifications indicative of the estimated mental state. The notifications may be outputted to the user as a visual alert (e.g., a virtual image displayed by a femtoimager 130), an audio alert, a notification on an accessory device 218, or another output mechanism. The alert may be directed to the user having the estimated abnormal mental condition or to other individuals among the user's friends, family, medical providers, or other specified connection. The notification module 230 may further send an output to the electronic contact lens 110 or other external device to initiate an automated action in response to detecting certain mental states. For example, when driving a vehicle, the notification module 230 may cause a steering wheel to shake in response to detecting that the driver is overly fatigued. In some cases, where the vehicle has autonomous driving capabilities, the notification module 230 may cause the vehicle to safely come to a stop in response to detecting an abnormal mental condition. If the user has not yet started the vehicle, the notification module 230 may send a command to the vehicle that prevents the vehicle from starting (e.g., in the case of detecting intoxication or extreme fatigue). In other cases, the notification module 230 may be linked to a machine being operated by a machine operator, and the notification module 230 may cause the machine to shut down responsive to detecting an abnormal mental condition. In yet further examples, a light intensity of a display or ambient lighting may be adjusted in response to detecting an abnormal mental condition affected by light intensity such as migraines.

Figure 3:
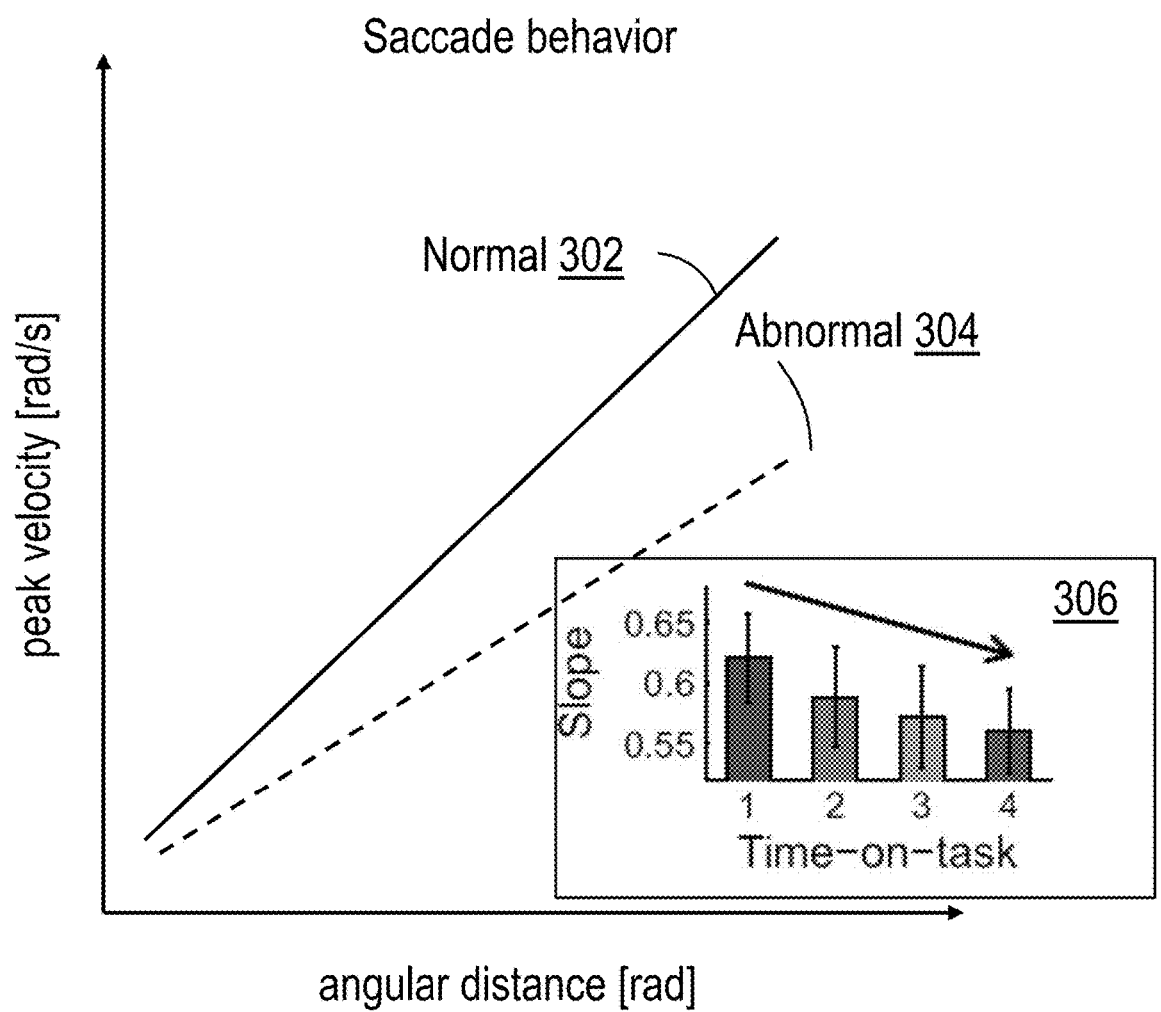
FIG. 3 is a diagram illustrating a relationship between slope of a saccadic main sequence and mental state.

FIGS. 3-11 illustrate various examples of eye motion parameters and their relationship to mental state. FIG. 3 is a plot characterizing a set of saccades under normal conditions (line 302) and a set of saccades under abnormal (e.g., fatigued) conditions (line 304). In each data set, the plotted best fit lines 302, 304 approximate the peak angular velocities (rad/s) over a range of angular distances (rad). This relationship is referred to as the saccadic main sequence. The slope of the saccadic main sequence characterizes how the peak angular velocity changes for saccades of different angular distances. In both plots 302, 304, the peak angular velocity generally increases for saccades of greater angular distance (i.e., the slope of the main sequence is positive). However, the slope will generally decrease as a subject becomes more fatigued, as indicated by the slope of line 304 relative to the slope of line 302.

The inset 306 in FIG. 3 plots the slope of the saccadic main sequence over a period of time when the subject is focused on a fatigue-inducing task. Here, the slope of the saccadic main sequence decreases as the time-on-task increases and the subject becomes more fatigued. This relationship is further described in Di Stasi, Leandro L., et al. "Microsaccade and drift dynamics reflect mental fatigue." *European Journal of Neuroscience* 38.3 (2013): 2389-2398.

The relationship illustrated in FIG. 3 can be used to detect fatigue or another abnormal mental condition that has a similar effect. In this example, the baseline parameter may comprise the slope of the main sequence estimated from sensor measurements captured over a statistically significant time period. The specific slope may vary for different individuals and in different contexts, and thus multiple different baselines may be estimated having varying slopes. The estimation module 228 can compare a current parameter (the slope of the main sequence estimated from a current set of sensor measurements) to a relevant baseline to detect a substantial decrease that is indicative of an abnormal mental condition.

Figure 4A:
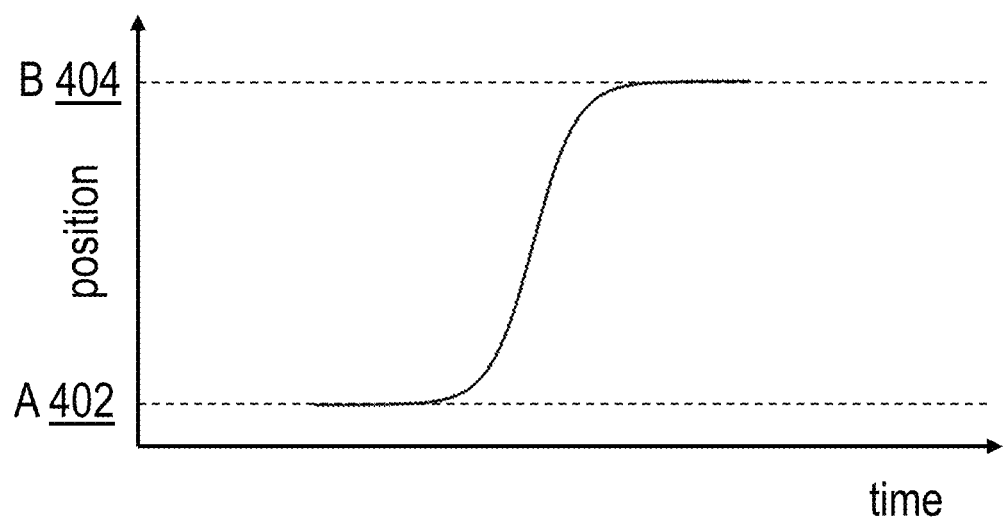
FIG. 4A is a diagram illustrating changes in position and velocity of an eye during a single saccade.
Figure 4A:
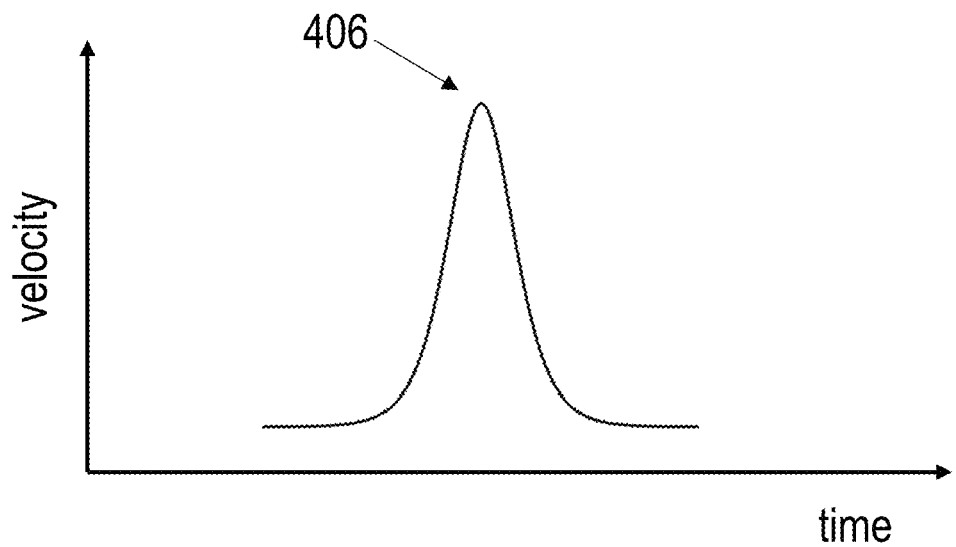
Figure 4B:
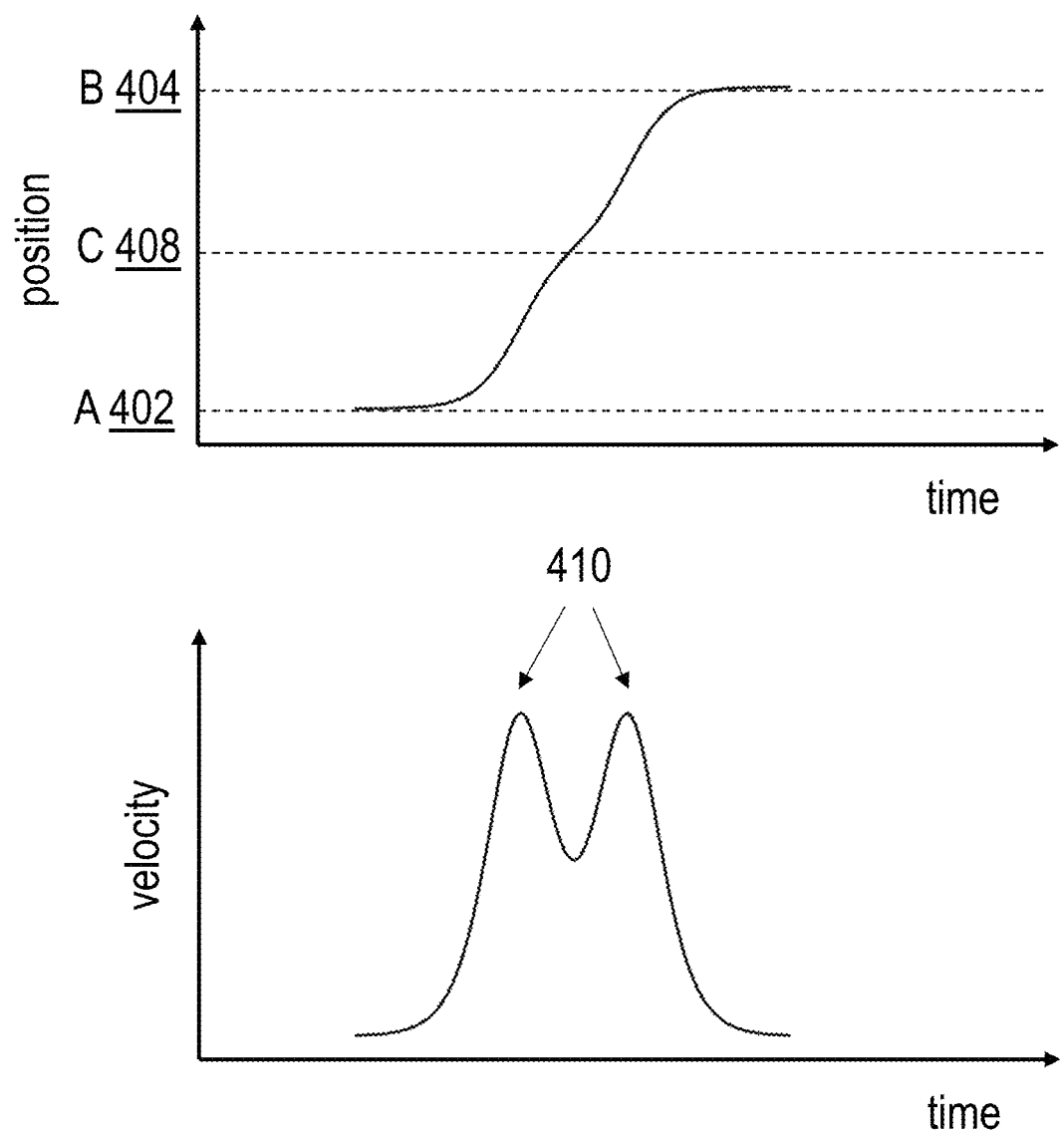
FIG. 4B is a diagram illustrating changes in position and velocity of an eye during a overlapping saccade.
Figure 4C:
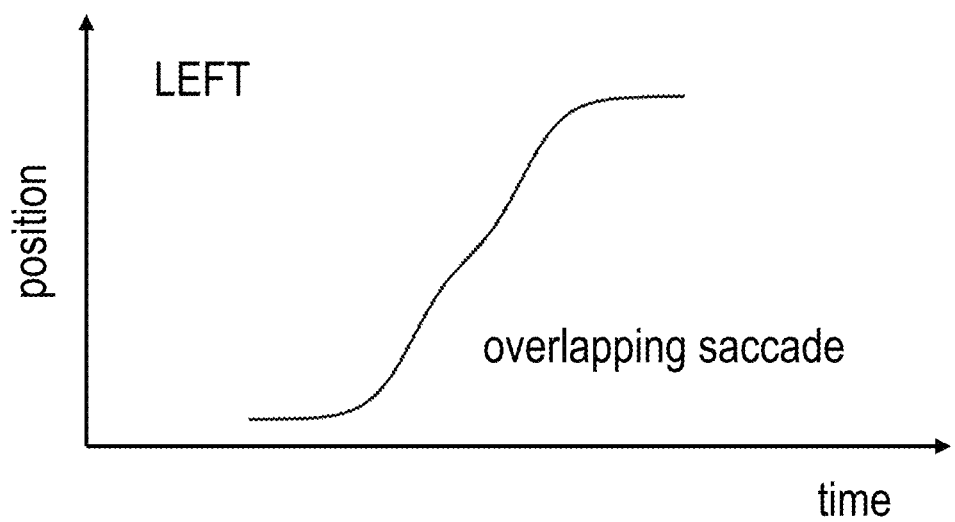
FIG. 4C is a diagram illustrating monocular changes in position during a concurrent single and overlapping saccade.
Figure 4C:
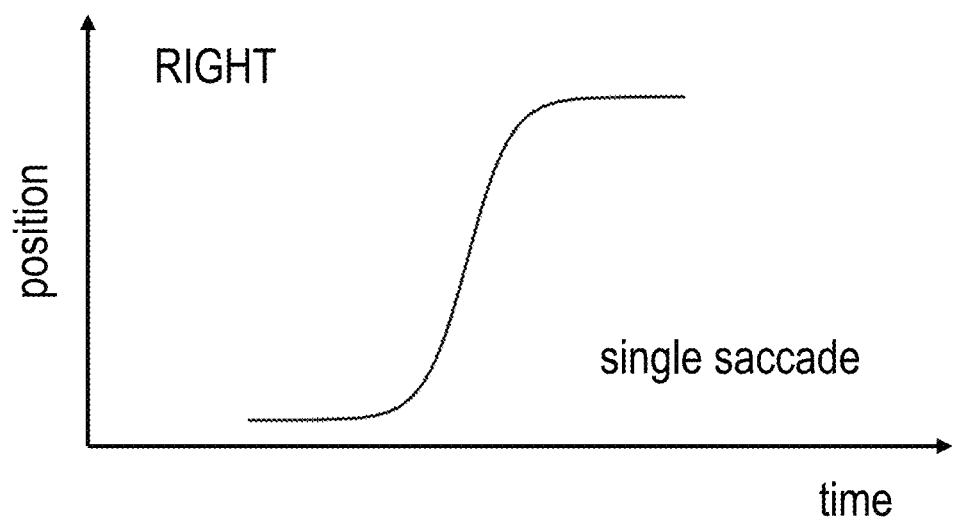

FIGS. 4A-C illustrate changes in position and velocity of the eye over time during a single saccade and during overlapping saccades. In the single saccade shown in FIG. 4A, the eye rapidly moves from position A 402 to position B 404 in a single motion characterized by a single spike 406 in velocity. In contrast, in the overlapping saccade shown in FIG. 4B, the eye movement from position A 402 to position B 404 is broken into two overlapping saccades of shorter distances in which the second saccade begins before the eye comes to rest. The overlapping saccade is characterized by a pair of velocity spikes 410 with a brief dip in velocity occurring in between them. FIG. 4C plots the positions of the left and right eyes during a saccade pattern in which the left eye performs an overlapping saccade and the right eye performs a single saccade.

Under normal conditions, it is generally expected for single saccades to occur much more frequently than overlapping saccades and for both eyes to move consistently with each other. However, under fatigued conditions or other abnormal mental states, overlapping saccades become more prevalent and the eyes may exhibit saccade motions that are inconsistent with each other (e.g., as shown in FIG. 4C). These relationships are described in further detail in Bahill, A. Terry, and Lawrence Stark. "Overlapping saccades and glissades are produced by fatigue in the saccadic eye movement system." *Experimental neurology* 48.1 (1975): 95-106, and Bahill, A. Terry, Michael R. Clark, and Lawrence Stark. "The main sequence, a tool for studying human eye movements." *Mathematical biosciences* 24.3-4 (1975): 191-204.

Therefore, a useful baseline parameter may be based on the rate of single saccades, the rate of overlapping saccades, a ratio between single and overlapping saccades, a difference in saccade patterns between the eyes, or some other related metric that characterizes this change in motion pattern. The estimation module 228 can compare a current parameter (e.g., a metric describing the recently observed saccades) to this baseline to detect changes that are indicative of an abnormal mental condition.

Figure 5:
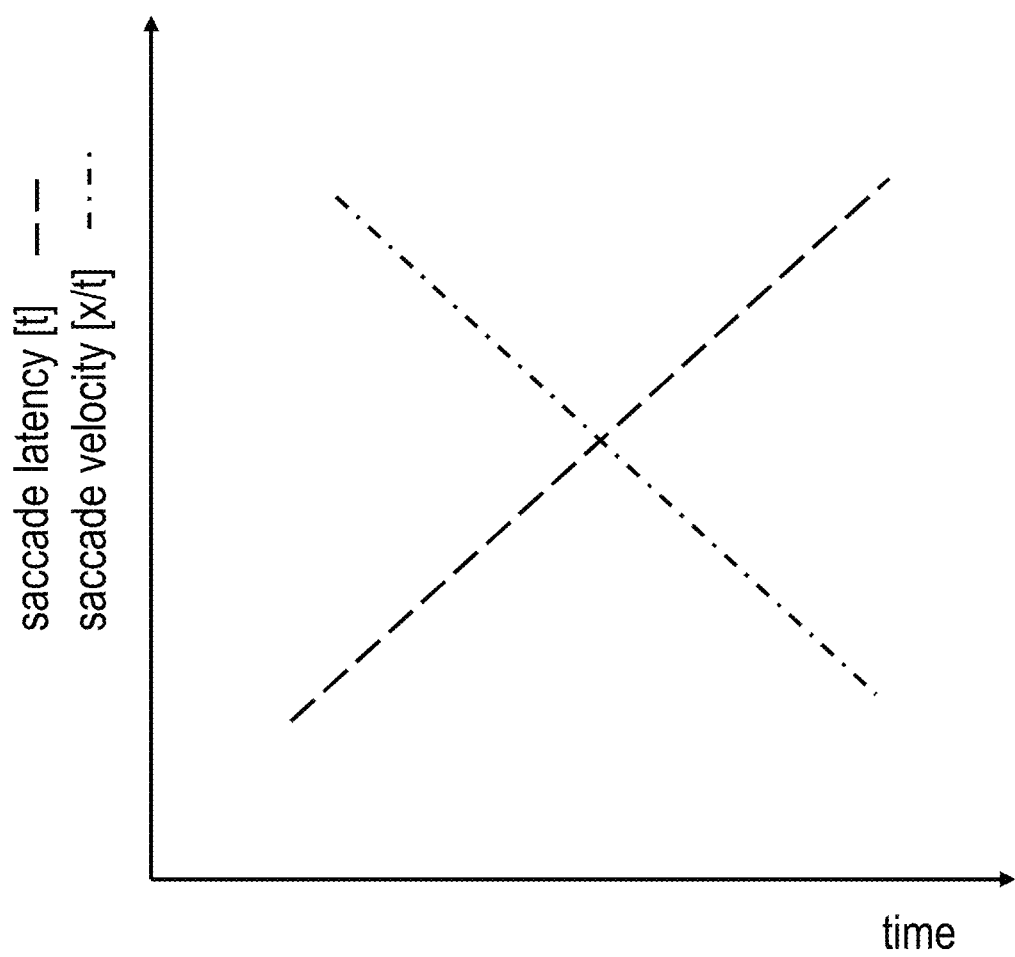
FIG. 5 is a diagram illustrating relationships between saccade latency, saccade velocity, and mental state.

FIG. 5 illustrates a plot of saccade latency (t) and saccade velocity (x/t) as fatigue of a subject increases over time. Here, it is shown that with increasing fatigue, the saccade latency tends to increase while the saccade velocity tends to decrease. This relationship is further described in De Gennaro, Luigi, et al. "Oculomotor impairment after 1 night of total sleep deprivation: a dissociation between measures of speed and accuracy." *Clinical Neurophysiology* 111.10 (2000): 1771-1778. Thus, in this example, the saccade latency, saccade velocity, or some combination (e.g., a ratio) can be estimated as a baseline parameter for a subject, and a substantial change can be detected by the estimation module 228 to indicate an abnormal mental condition such as a fatigue.

Figure 6:
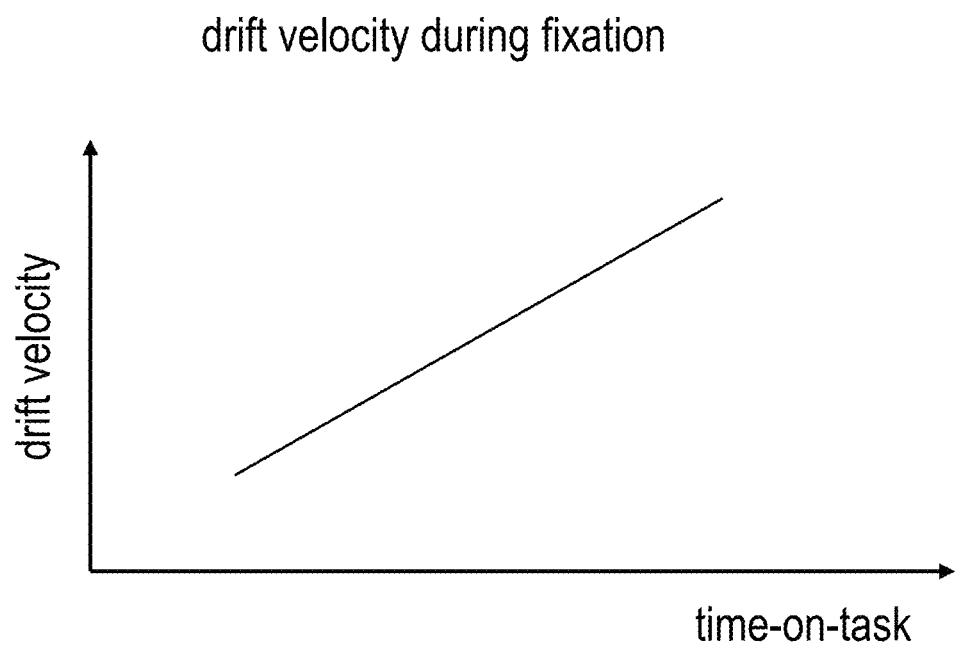
FIG. 6 is a diagram illustrating a relationship between drift velocity and mental state.

FIG. 6 illustrates how drift velocity of the eye changes with increasing fatigue levels. Here, the drift velocity is measured when the subject attempts to focus gaze on a fixed point (i.e., maintain a zero or very low drift velocity). With increasing fatigue, the subject's ability to maintain a stable gaze direction decreases as characterized by the increasing drift velocity. This relationship is further described in Di Stasi, Leandro L., et al. "Microsaccade and drift dynamics reflect mental fatigue." *European Journal of Neuroscience* 38.3 (2013): 2389-2398. Thus, in this example, a baseline drift velocity may be obtained for a subject under normal conditions and a substantial increase in drift velocity from the baseline may be detected as an indicator of an abnormal mental condition such as fatigue.

Figure 7A:
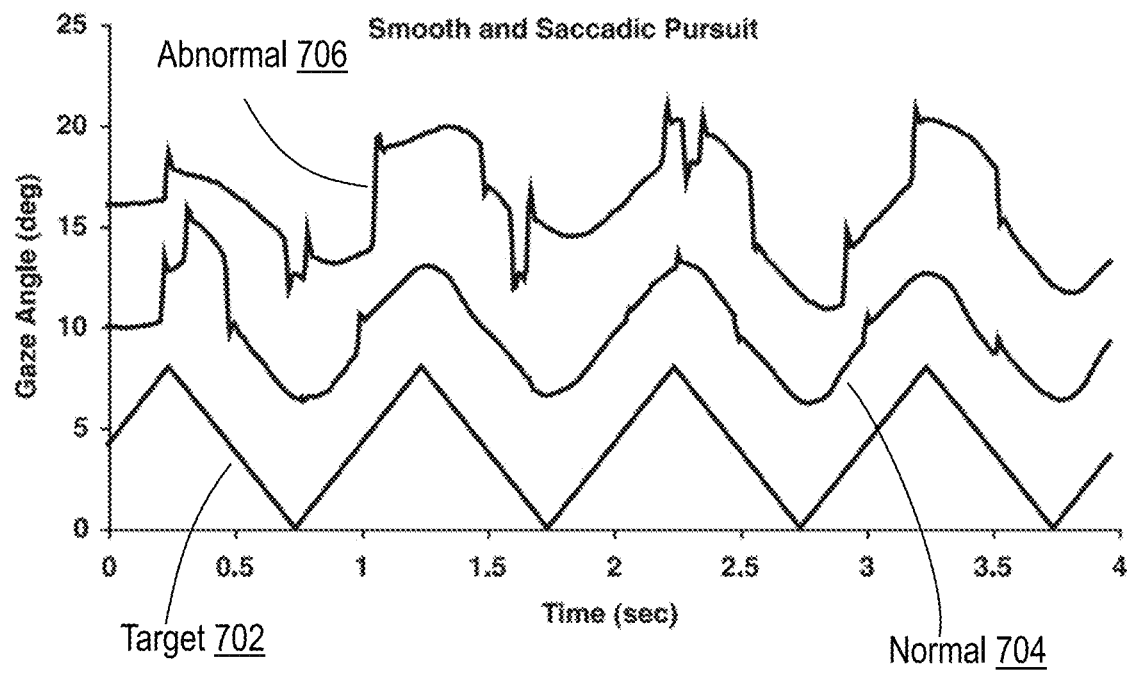
FIG. 7A is a diagram illustrating motion of the eye during target tracking under normal and abnormal mental states.

FIG. 7A illustrates changes in gaze angle of a subject under normal and abnormal mental conditions as the subject executes a smooth pursuit in which the subject attempts to adjust gaze direction to track a moving target 702. This relationship is further described in Rubenzer, Steven J., and Scott B. Stevenson. "Horizontal gaze nystagmus: a review of vision science and application issues." *Journal of forensic sciences* 55.2 (2010): 394-409. Here, it can be seen that under normal conditions 704, the subject's gaze direction accurately tracks the target location 702. However, under abnormal conditions 706, the subject's gaze direction is less smooth and contains abrupt changes in gaze angle. Thus, in this case, the estimation module 228 may detect an abnormal mental condition by detecting a high measure of inaccuracy in the subject's eye tracking relative to the baseline accuracy. Here, the level of inaccuracy may be identified based on various metric such as average distance between the target motion and the gaze direction motion, latency between the target motion and the gaze direction motion, presence of discontinuities, or other characteristics.

Figure 7B:
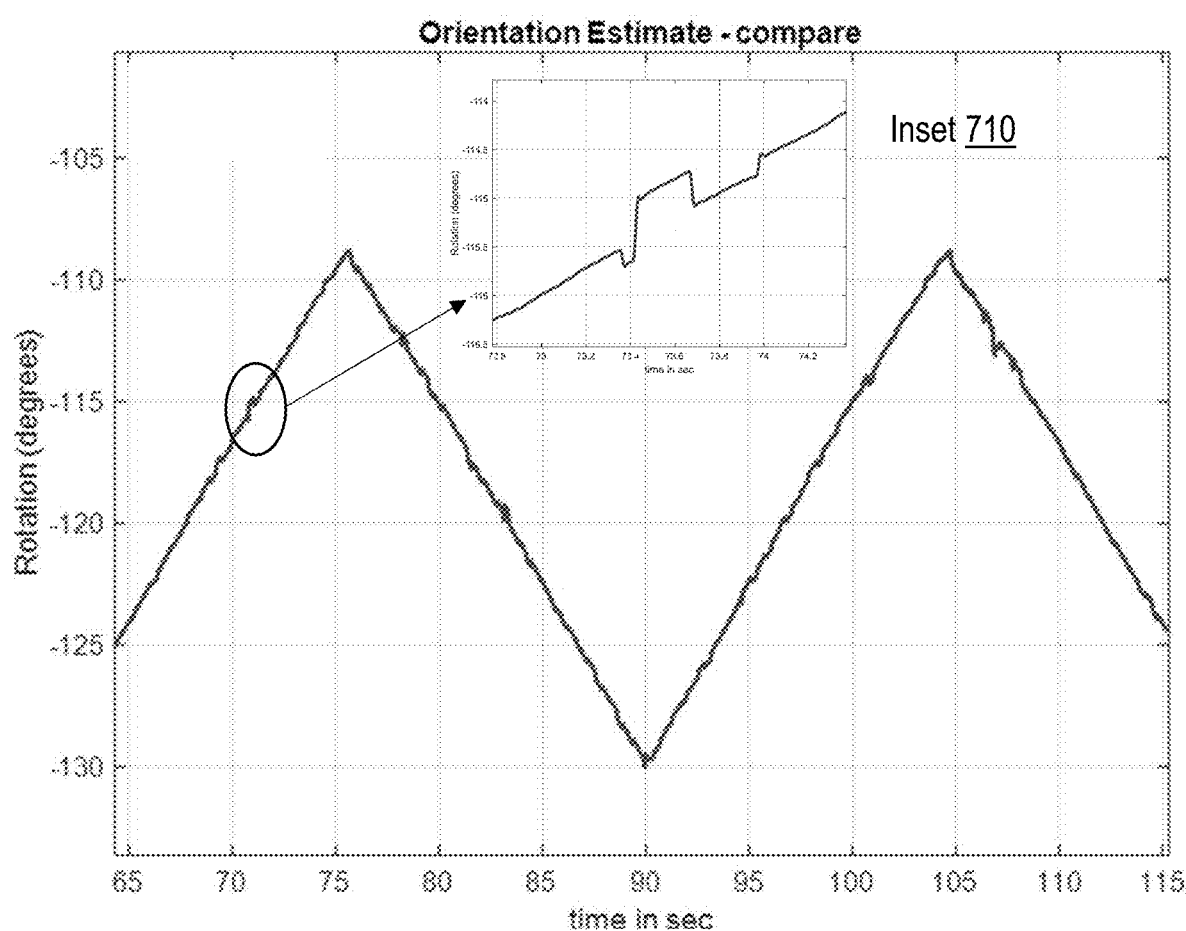
FIG. 7B is a plot of eye motion during a target tracking as obtained from an electronic contact lens.

FIG. 7B is a plot of rotation angle over time captured by an actual electronic contact lens 110 similar to the one described herein. This data was captured when the user was asked to follow a target moving horizontally according to a triangle wave function, similar to the movement of the target in FIG. 7A. Here, the user exhibits a normal mental condition and the data from the electronic contact lens 110 is a relatively smooth triangle wave. The small deviations (magnified in the inset 710) represent microsaccades that occur around the target. While the microsaccades are normal eye movements, the presence of much larger saccades (like those shown in FIG. 7A) would be indicative of an abnormal condition.

FIG. 8 is a chart comparing normal (baseline) and abnormal saccade rates (saccades per second) and blink rate (blinks per second) together with their standard deviations (SD). As shown, under abnormal conditions, the subject tends to exhibit fewer saccades per second and more blinks per second relative to normal conditions. This relationship is further described in Di Stasi, Leandro L., et al. "Effects of driving time on microsaccadic dynamics." *Experimental brain research* 233.2 (2015): 599-605. Thus, in this example, the saccade rate, blink rate, or a combination thereof may be used as a baseline parameter and significant deviations may be detected as being indicative of an abnormal mental condition.

Figure 9:
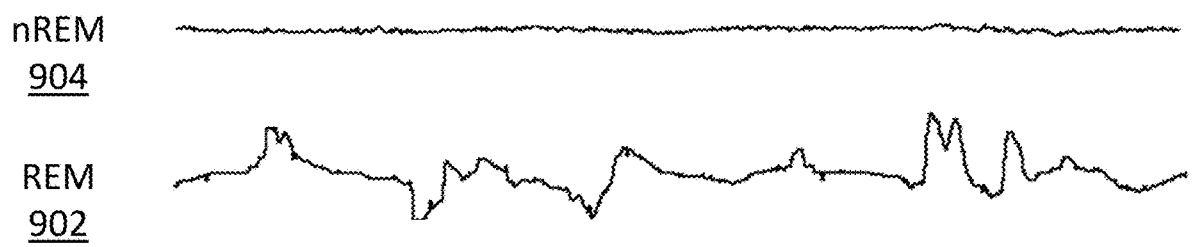
FIG. 9 illustrates a set of plots of eye position over time indicative of a user's sleep state.
Figure 10:
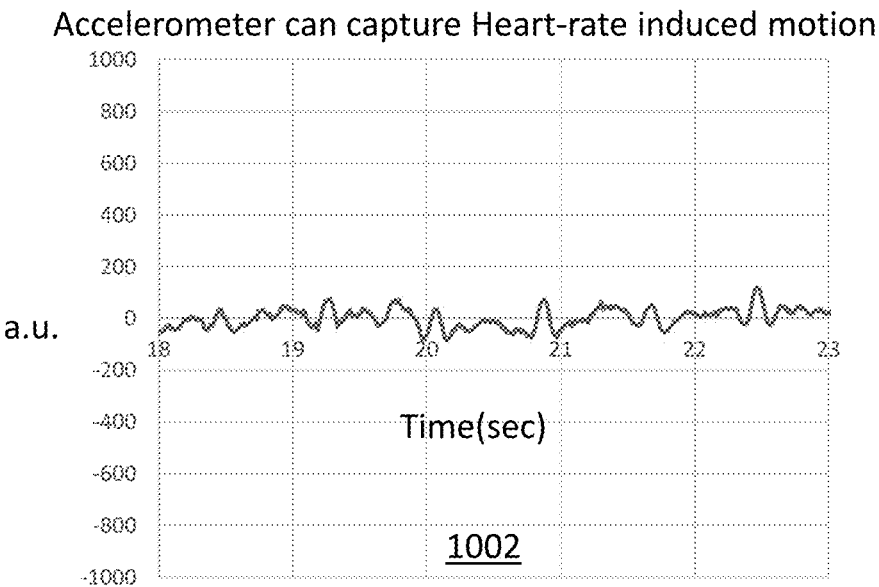
FIG. 10 illustrates time-domain and frequency domain plots of acceleration over time as captured from an electronic contact lens that are indicative of heart rate.
Figure 10:
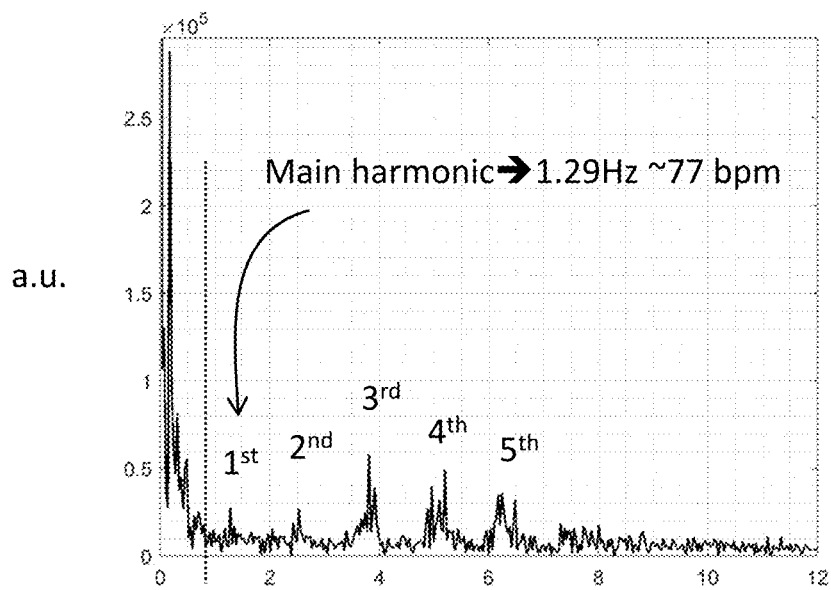
Figure 11:
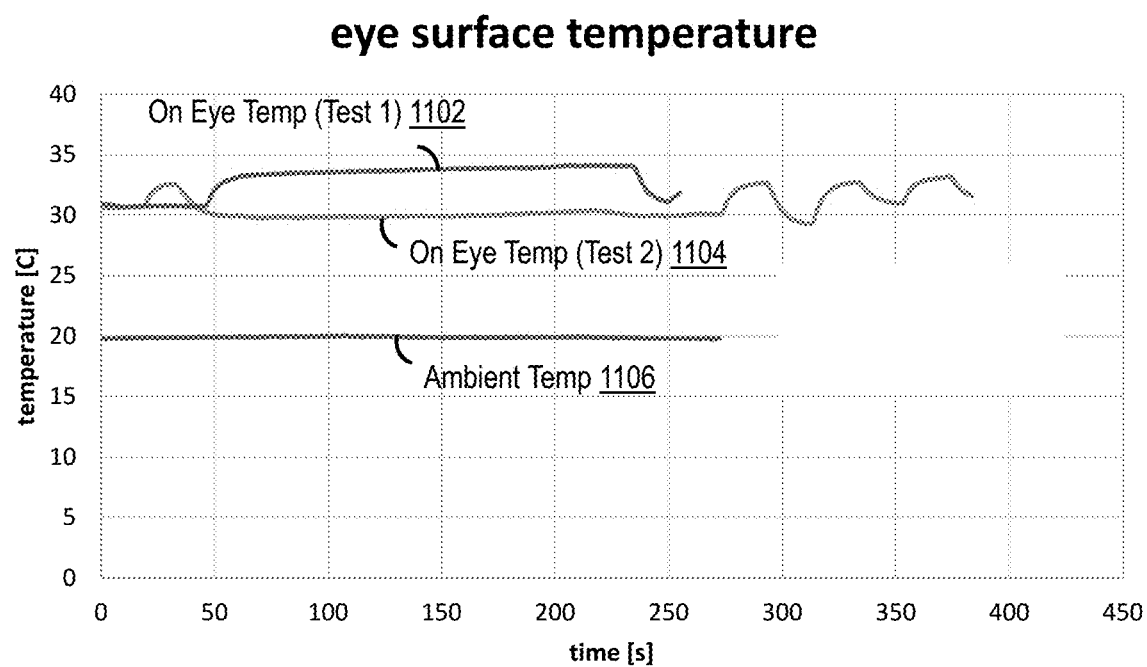
FIG. 11 illustrates plots of temperature over time as captured by an electronic contact lens under varying conditions.

FIGS. 9-11 illustrate example data associated with sleep patterns that can be captured and analyzed by an electronic contact lens 110. Here, the electronic contact lens system 200 can measure the user's eye motion (FIG. 9), heart rate (FIG. 10), and body temperature (FIG. 11), each of which can be used alone or in combination to estimate a sleep state of the user and estimate the amount of time the user spends in each sleep state. Changes in the user's sleep pattern (i.e., deviations from the baseline) may be an indicator of an abnormal mental state. This tracking may also be useful to provide the user with feedback regarding their sleep health or to present specific recommendations to improve sleep health.

FIG. 9 illustrates example plots showing eye position over time while the subject is in a rapid-eye-movement (REM) sleep cycle 902, and when the subject is in a non-rapid-eye-movement (nREM) sleep cycle 904. These motions are further described in Conduit, Russell, et al. "Spontaneous eyelid movements during human sleep: a possible ponto-geniculo-occipital analogue?." *Journal of sleep research* 11.2 (2002): 95-104. The motions can be sensed by the electronic contact lens 110 even when the eyes are closed.

FIG. 10 illustrates a time-domain plot 1002 and a frequency-domain plot 1004 of linear acceleration measured from a human eye by an accelerometer of the electronic contact lens 110. The subject's heart rate can be estimated using different kinds of algorithms such as by proper harmonics analysis in the acceleration spectrum occurring within the normal range of heart rates. In the illustrated plots, the algorithm ignores very low frequency peaks (less than 0.5 Hz) and sorts multi-peaks including main and higher order harmonics ($1^{st}$, $2^{nd}$, $3^{rd}$ and $4^{th}$ order) to best estimate the main harmonic representing average heart rate over a window of time (e.g. 5 sec). Here, for example, a heart rate of 77 beats per minute (corresponding to 1.29 Hz) can be estimated based on the captured eye movement. Using this technique, a baseline heart rate can be captured for the individual over time and deviations in the normal heart rate can be detected as an indicator of an abnormal mental (or in this case, physical) condition. Heart rate captured during sleep may also provide a good indicator of sleep quality.

FIG. 11 illustrates various plots of temperature measurements that were obtained by a temperature sensor of the electronic contact lens 110 over time captured while the subject is performing different patterns of opening and closing the eye. During a first period represented by curve 1102, the subject closed the eye and kept it closed for several minutes. During a second period represented by curve 1104, the subject repeatedly closed the eye for a short time period (approximately 30 seconds) and then opened it. The ambient temperature 1106 is also plotted, as measured by an external sensor. These plots demonstrate that temperature detected by the electronic contact lens 110 increases when the eye closes and eye closures and opening can thus be sensed based on the measured temperature. This information can be used to detect sleep periods indicative of the user's sleep quality. Furthermore, because the measured eye temperature tracks closely to core body temperature, temperature measurements may be used alone or in combination with other captured information to detect changes in the subject's body temperature (relative to a baseline) that may be further indicative of an abnormal mental or physical condition.

Figure 12:
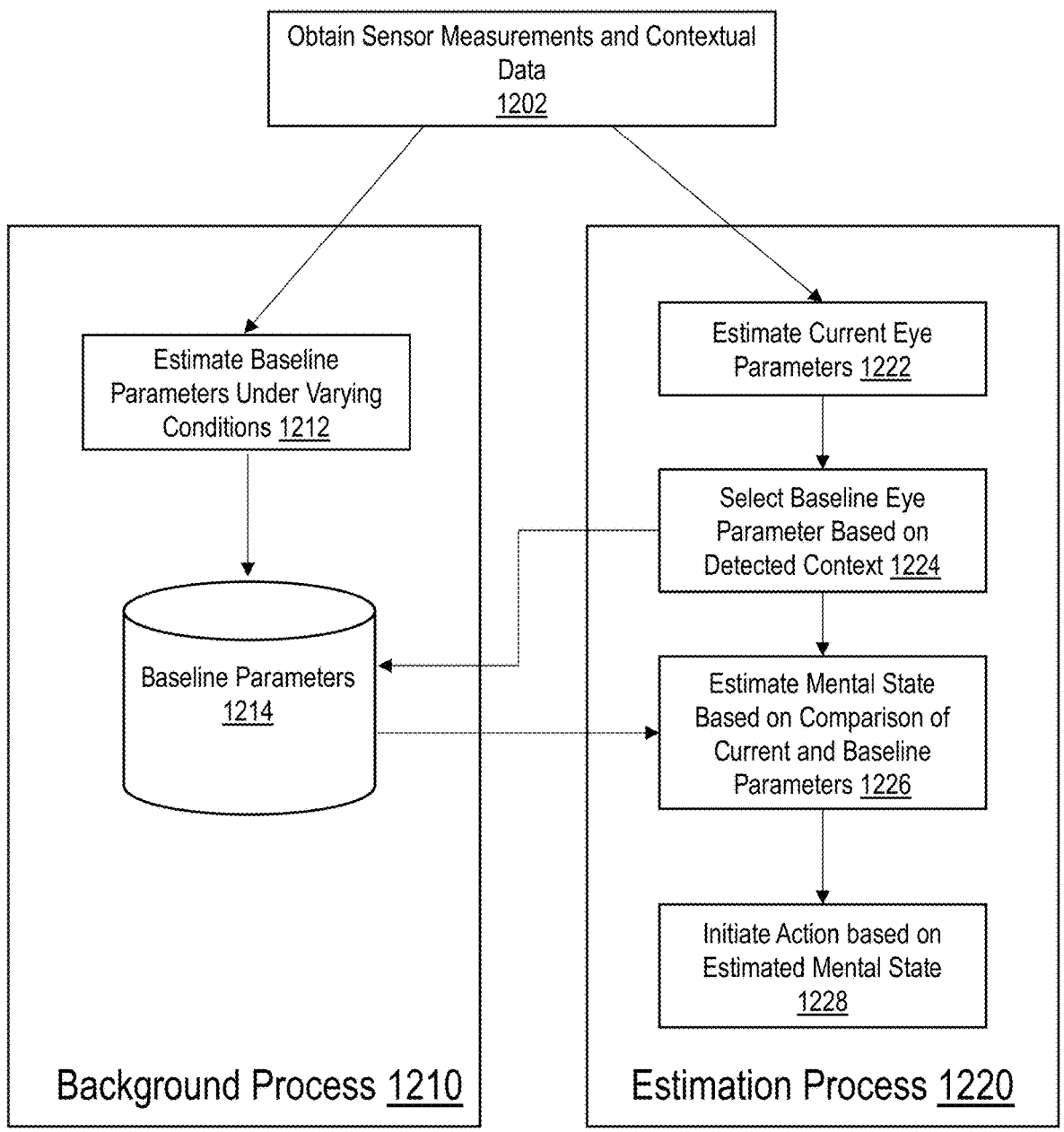
FIG. 12 is a flowchart illustrating an example embodiment of a process for estimating a mental state based on baseline and current parameters derived from sensor measurements of an electronic contact lens.

FIG. 12 illustrates an example embodiment of a process for estimating a mental condition of a subject based on tracked eye movements using sensor measurements from an electronic contact lens 110. The process includes a background process 1210 and a estimation process 1220. The background process 1210 operates to estimate baseline motion parameters that can be applied by the estimation process 1220 to detect deviations from the baselines that are indicative of an abnormal mental condition. The baseline motion parameters may be universal parameters (not specific to subject or context), subject-specific parameters (estimated from sensor measurements from a specific subject), and/or context-specific (estimated from sensor measurements captured in a specific context).

In the background process 1210, the electronic contact lens 110 obtains 1202 sensor measurements and contextual data. This data is analyzed over a relatively long time period (e.g., days, weeks, months, or even years) to estimate 1212 baseline parameters (which may include user-specific and/or context-specific baseline parameters). The baseline parameters are stored to a baseline parameter store 1214 together with relevant contextual data. The baseline parameter store 1214 may furthermore store universal baseline parameters obtained from external sources that are not necessarily estimated from sensor measurements captured from an electronic contact lens 110.

In the estimation process 1220, one or more current parameters are estimated 1222 from a set of recent sensor measurements and contextual data. The recent sensor measurements are captured over a relatively short time period (e.g., seconds or minutes) compared to the time period used to compute the baseline parameters. The current parameters may be estimated using any of the same techniques described above for generating the baseline parameters. Based on the associated contextual data, a lookup is performed in the baseline parameter store 1214 to select 1224 a baseline parameter relevant to the currently detected context. For example, if a subject is currently driving a vehicle at night, the estimation process 1220 obtains a baseline parameter estimated from sensor measurements captured under the same or similar context. A mental state of the subject is estimated 1226 based on a comparison of the current parameter to the baseline parameter. The electronic contact lens system 200 initiates 1228 an action based on the estimated mental state. For example, the electronic contact lens system 200 may initiate a visual or audio alert indicative of the estimated mental state.

Figure 13:
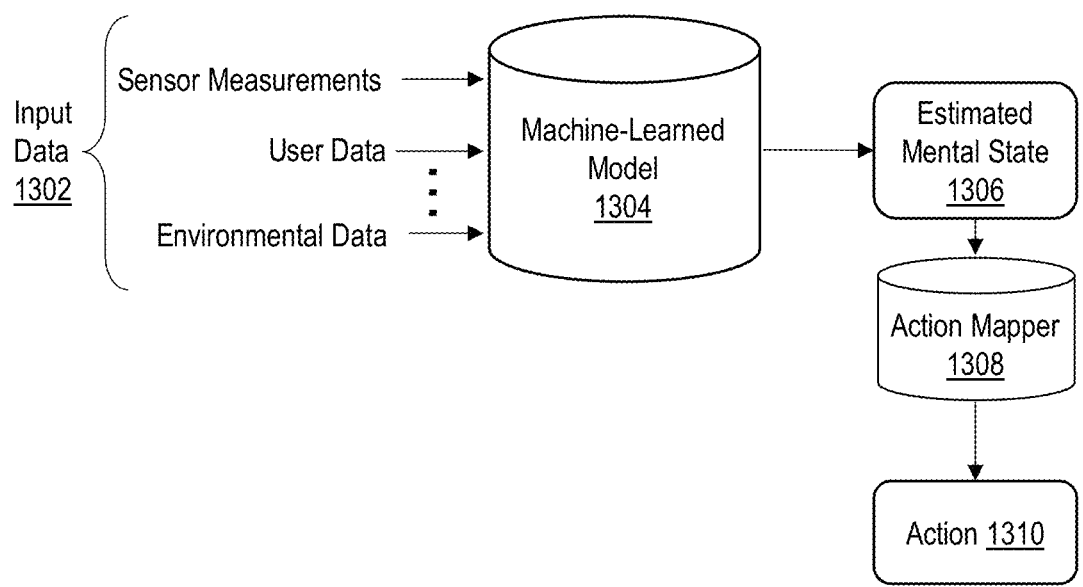
FIG. 13 is a flowchart illustrating an example embodiment of a process for estimating a mental state based on sensor measurements from an electronic contact lens using a machine-learned model.

FIG. 13 illustrates another technique for estimating a mental condition based on sensor measurements from an electronic contact lens 110. Here, input data 1302 comprising sensor measurements and contextual data (e.g., user data, environmental data, etc.) is inputted to a machine-learned model 1304 that maps the inputs to an estimated mental state 1306. The estimated mental state 1306 may then be mapped to a specific action 1310 based on data stored in an action mapper database 1308. The electronic contact lens system 200 then carries out the selection action.

In this embodiment, the machine-learned model 1304 may be trained using a large dataset of sensor measurements captured in varying contexts described by the contextual data. In a supervised training process, the data may be labeled with a corresponding mental condition that the subject matter is experiencing at the time of capture. Alternatively, in an unsupervised training process, the input data is clustered into clusters each representing normal mental states. When applying the machine-learned model 1304, an abnormal state can then be detected when the current input data has a statistically significant deviation from the learned clusters.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

Alternate embodiments are implemented in computer hardware, firmware, software and/or combinations thereof. Implementations can be implemented in a computer program product tangibly embodied in a non-transitory computer-readable storage device for execution by a programmable processor; and method steps can be performed by a programmable processor executing a program of instructions to perform functions by operating on input data and generating output. Embodiments can be implemented advantageously in one or more computer programs that are executable on a programmable system including at least one programmable processor coupled to receive data and instructions from and to transmit data and instructions to, a data storage system, at least one input device and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files. Any of the foregoing can be supplemented by, or incorporated in, ASICs (application-specific integrated circuits) and other forms of hardware.

The invention claimed is:

1. A method for estimating a mental state of a subject wearing an electronic contact lens, the method comprising:
obtaining, under each of a set of different detected conditions associated with the subject, first sensor measurements from one or more motion sensors integrated in the electronic contact lens worn by the subject;
estimating from the first sensor measurements, a set of baseline eye motion parameters characterizing eye motion of the first subject, the set of baseline eye motion parameters each corresponding to one of the different detected conditions;
obtaining, for an evaluation time period, second sensor measurements from the one or more motion sensors integrated in the electronic contact lens worn by the subject;
estimating from the second sensor measurements, a current eye motion parameter characterizing the eye motion of the subject during the evaluation time period;
estimating a condition associated with the subject during the evaluation time period;
selecting, from the set of stored baseline eye motion parameters, a selected baseline eye motion parameter corresponding to the condition of the subject during the evaluation time period; and
estimating a mental state of the subject based on a comparison of the current eye motion parameter and the selected baseline eye motion parameter; and
initiating an action based on the estimated mental state.

2. The method of claim 1, wherein estimating the current eye motion parameter comprises:
detecting one or more occurrences of a predefined type of eye movement based on the second sensor measurements; and
estimating the current eye motion parameter from the one or more occurrence of the predefined type of eye movement.

3. The method of claim 2, wherein the predefined type of eye movement includes one of a saccade, a microsaccade, a fixation period, a smooth pursuit, and a drift.

4. The method of claim 2, wherein the current eye motion parameter represents a frequency of the predefined type of eye movement, an amplitude of the predefined type of eye movement, a time period associated with the predefined type of eye movement, or a count of the predefined type of eye movement.

5. The method of claim 1, wherein estimating the current eye motion parameter comprises:
identifying a set of saccades of the eye associated with the current time period; and
estimating a rate of change of a function approximating a relationship between saccade angular distance and saccade peak velocity for the set of saccades.

6. The method of claim 1, wherein estimating the condition comprises estimating a physical state of the subject.

7. The method of claim 6, wherein estimating the physical state of the subject comprises at least one of:
estimating whether the subject is sitting, standing, or laying down;
estimating if the subject is driving a vehicle; and
estimating whether the subject is indoors or outdoors.

8. The method of claim 1, wherein estimating the condition comprises estimating an environmental condition associated with an environment where the subject is located.

9. The method of claim 8, wherein estimating the environmental condition comprises at least one of:
estimating a time of day;
estimating a level of visual stimulus in a vicinity of the subject.

10. The method of claim 1, wherein estimating the condition comprises:
obtaining an image of an environment of the subject during the evaluation time period from a femtoimager integrated with the electronic contact lens; and
performing an image analysis of the image to estimate the condition.

11. The method of claim 1, wherein estimating the condition comprises:
obtaining at least a subset of the second sensor measurements when the eye of the subject is closed.

12. The method of claim 1, wherein obtaining the second sensor measurements comprises:
sensing torsional rotation of the eye.

13. The method of claim 1, wherein estimating the mental state comprises estimating at least one of: a fatigue level, a intoxication level, trauma level, and an illness.

14. The method of claim 1, wherein initiating the action comprises:
causing a femtoimager of the contact lens to project to project a visual alert into the eye.

15. The method of claim 1, wherein initiating the action comprises:
causing an audio output device to output an audio alert.

16. The method of claim 1, wherein the electronic contact lens includes at least one of: a gyroscope, an accelerometer, a magnetometer, a temperature sensor, an imager, and a light sensor.

17. The method of claim 1, wherein the electronic contact lens comprises an integrated accelerometer, an integrated gyroscope, and an integrated magnetometer, wherein obtaining the second sensor measurements comprises:
obtaining gyroscope data, magnetometer data, and accelerometer data; and
filtering the gyroscope data to reduce drift in the gyroscope data based on the magnetometer data and the accelerometer data.

18. The method of claim 1, wherein the electronic contact lens comprises an integrated gyroscope and an integrated temperature sensor, wherein obtaining the second sensor measurements comprises:
obtaining gyroscope data and temperature data; and
filtering the gyroscope data to reduce temperature bias based on the temperature data.

19. A method for estimating a mental state of a subject wearing an electronic contact lens, the method comprising:
obtaining first sensor measurements from one or more motion sensors integrated in the electronic contact lens worn by the subject;
estimating from the first sensor measurements, a baseline eye motion parameter characterizing a baseline eye motion of the first subject;
obtaining, for an evaluation time period, second sensor measurements from the one or more motion sensors integrated in the electronic contact lens worn by the subject;
estimating from the second sensor measurements, a current eye motion parameter characterizing eye motion of the first subject during the evaluation time period;
estimating a mental state of the subject based on a comparison of the baseline eye motion parameter and the current eye motion parameter; and
initiating an action based on the estimated mental state.

20. A method for estimating a mental state of a subject wearing an electronic contact lens, the method comprising:
obtaining, for a baseline time period, first sensor measurements from one or more motion sensors integrated in the electronic contact lens worn by the subject;
obtaining, for an evaluation time period, second sensor measurements from the one or more motion sensors integrated in the electronic contact lens worn by the subject;
inputting the first sensor measurements and the second sensor measurements into a machine-learned model that is trained to map the first and second sensor measurements to an estimated mental state; and
initiating an action based on the estimated mental state.

* * * * *